US011376089B1

(12) United States Patent
Lance et al.

(10) Patent No.: US 11,376,089 B1
(45) Date of Patent: Jul. 5, 2022

(54) SURGICAL DRAPE FOR USE IN A CESAREAN DELIVERY

(71) Applicant: ORLANDO HEALTH, INC., Orlando, FL (US)

(72) Inventors: Teresa Lance, Orlando, FL (US); Neeraj Desai, Windmere, FL (US)

(73) Assignee: ORLANDO HEALTH, INC., Orlando, FL (US)

( * ) Notice: Subject to any disclaimer, the term of this patent is extended or adjusted under 35 U.S.C. 154(b) by 30 days.

(21) Appl. No.: 17/182,720

(22) Filed: Feb. 23, 2021

(51) Int. Cl.
*A61B 46/00* (2016.01)
*A61B 46/23* (2016.01)

(52) U.S. Cl.
CPC .............. *A61B 46/30* (2016.02); *A61B 46/23* (2016.02); *A61B 46/40* (2016.02); *A61B 2046/234* (2016.02)

(58) Field of Classification Search
CPC ......... A61B 46/30; A61B 46/40; A61B 46/23; A61B 2046/201; A61B 2046/205; A61B 2046/234; A61B 17/42
See application file for complete search history.

(56) References Cited

U.S. PATENT DOCUMENTS

| 3,423,277 | A | | 1/1969 | Dipner | |
|---|---|---|---|---|---|
| 3,799,161 | A | * | 3/1974 | Collins | ................. A61B 46/00 128/854 |
| 4,027,665 | A | * | 6/1977 | Scrivens | ................ A61B 46/00 128/854 |
| 5,592,952 | A | * | 1/1997 | Bohn | ..................... A61B 46/00 128/853 |
| 7,409,953 | B2 | | 8/2008 | Griesbach, III | |
| 8,011,371 | B2 | | 9/2011 | Rotolo | |
| 8,079,365 | B2 | | 12/2011 | Block et al. | |
| 9,278,166 | B2 | | 3/2016 | Czajka, Jr. et al. | |
| 2014/0258543 | A1 | | 9/2014 | Dalela | |
| 2017/0014199 | A1 | | 1/2017 | Schwartz et al. | |
| 2019/0142541 | A1 | | 5/2019 | Neis et al. | |
| 2019/0216565 | A1 | | 7/2019 | Menut et al. | |

OTHER PUBLICATIONS

U.S. Appl. No. 10/271,916, filed Apr. 30, 2019, Allen.
U.S. Appl. No. 10/265,133, filed Apr. 23, 2019, McClellan.
U.S. Appl. No. 10/188,474, filed Jan. 29, 2019, Jarrelle et al.
U.S. Appl. No. 10/111,724, filed Oct. 30, 2018, Schwartz et al.

* cited by examiner

*Primary Examiner* — Camtu T Nguyen
(74) *Attorney, Agent, or Firm* — Crowell & Moring LLP

(57) ABSTRACT

A surgical drape may include one or more of the following: a main portion, the main portion having a surgical opening, the surgical opening being configured to provide surgical access to a first target patient site; a window located adjacent to the surgical opening, the window including a transparent panel such that the window provides visual access to a second target patent site; and a flap having at least one edge secured to the main portion, where the flap includes a second edge that is movable such that the flap selectively covers the window.

8 Claims, 3 Drawing Sheets

SURGICAL DRAPE FOR USE IN A CESAREAN DELIVERY

TECHNICAL FIELD

The present disclosure relates to surgical drapes for use in a Cesarean delivery.

BACKGROUND

Surgical procedures are typically performed with a solid (non transparent) drape placed on top of a patient. The surgical drape is generally constructed of a material that prevents blood and other bodily fluids from permeating through the drapes. Openings may be selectively located to provide clinicians with physical access to the patient's body.

For example, drapes used in Cesarean deliveries (or "C-sections") include a main sheet of the drape substantially covering the mother's lower body. A surgical opening, which is optionally covered with an adhesive film before use, may be placed over the mother's abdomen. This opening may provide a surgeon with physical access such that delivery may occur through a surgical incision in the mother's abdomen and/or uterus.

While such drapes have been used with some success, the present disclosure relates to an improved surgical drape.

BRIEF DESCRIPTION OF THE DRAWINGS

The embodiments discussed herein may be better understood with reference to the following drawings and description. The components in the figures are not necessarily to scale. Moreover, in the figures, like-referenced numerals designate corresponding parts throughout the different views.

DETAILED DESCRIPTION

The present disclosure relates to surgical drapes for use in a Cesarean delivery. The following embodiments, and variations thereof, are advantageous for overcoming shortcomings of existing surgical drapes. For example, present surgical drapes designed for use with Cesarean deliveries provide physical or surgical access to a first target patient area (e.g., at the abdomen), but the remainder of the mother's lower body is covered. Such a design successfully creates a sterile and fluid barrier over the mother's lower body (which is desirable). However, a shortcoming of this design is that, without moving the drapes, the clinicians monitoring the mother cannot view areas of the mother's body beneath the drapes. The present embodiments overcome this shortcoming.

In particular, the present embodiments relate to a surgical drape that has a transparent window selectively located such that blood loss from the mother's body can be monitored visually. For example, some women experience moderate to severe bleeding from the uterus during a C-section. While a certain amount of bleeding is normal (e.g., an average C-section is associated with about four cups of blood loss), excess blood loss can be dangerous. The window included in the drapes discussed herein provides direct visual access to the vaginal region of the mother, which is often an area experiencing C-section blood loss. Advantageously, the blood loss can be monitored visually and problems may be identified quickly and easily. While the examples below are specifically tailored to C-section procedures, it is contemplated that the aspects discussed herein may be used with surgical drapes designed for other purposes.

Figure 1:
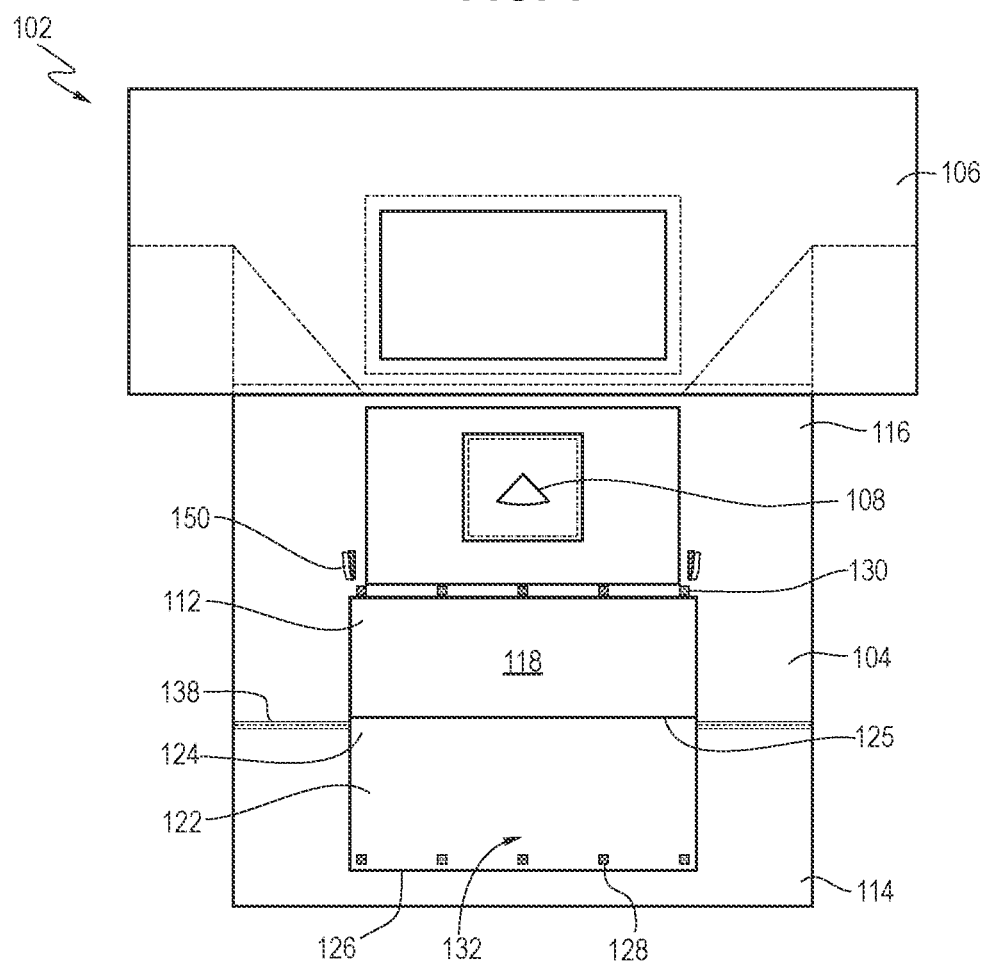
FIG. 1 is a top view of a surgical drape for use in a Cesarean delivery in accordance with certain aspects of the present disclosure.
Figure 2:
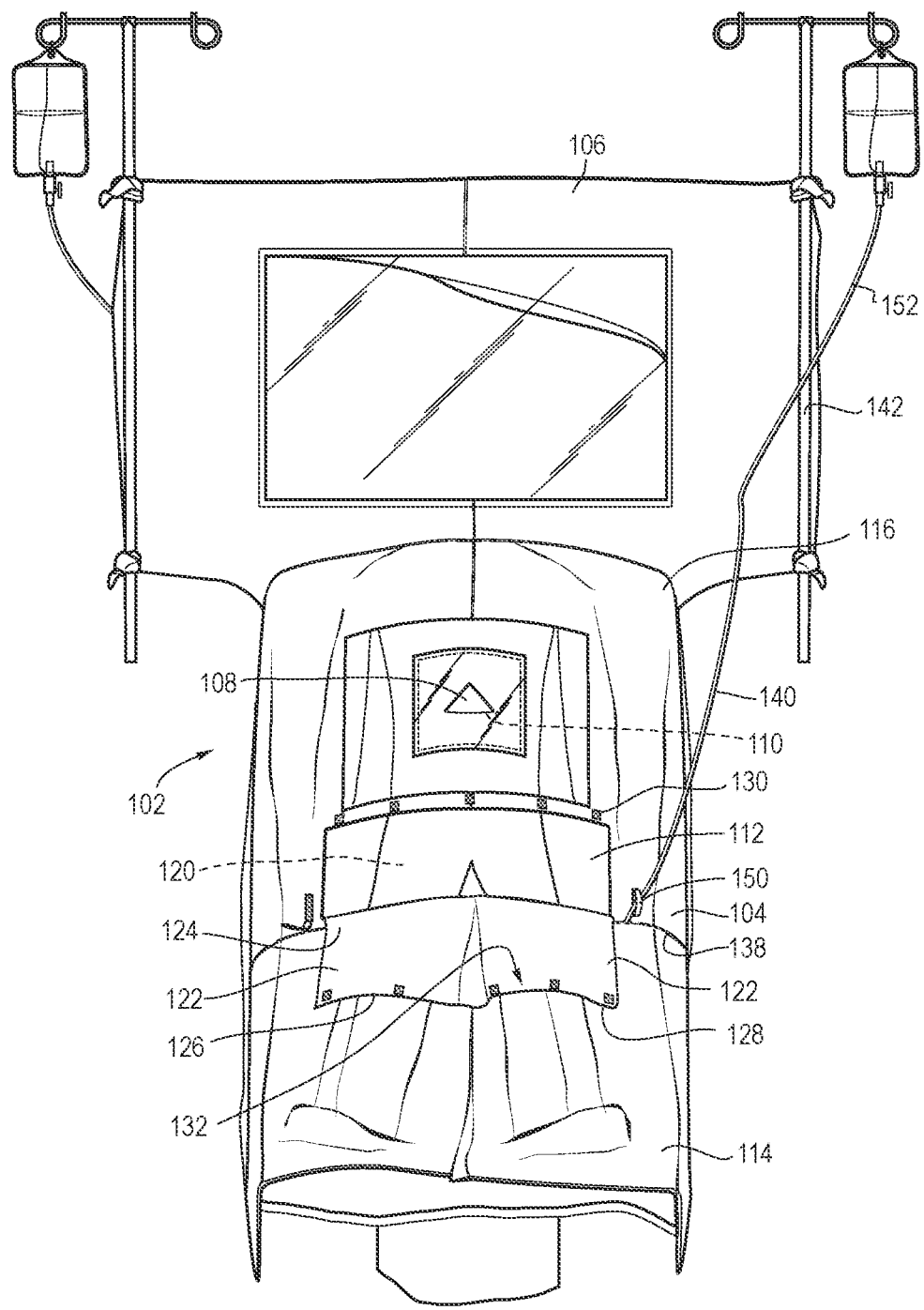
FIG. 2 is a first perspective view showing the drape from FIG. 1 located on top of a patient, such as during the Cesarean delivery.
Figure 3:
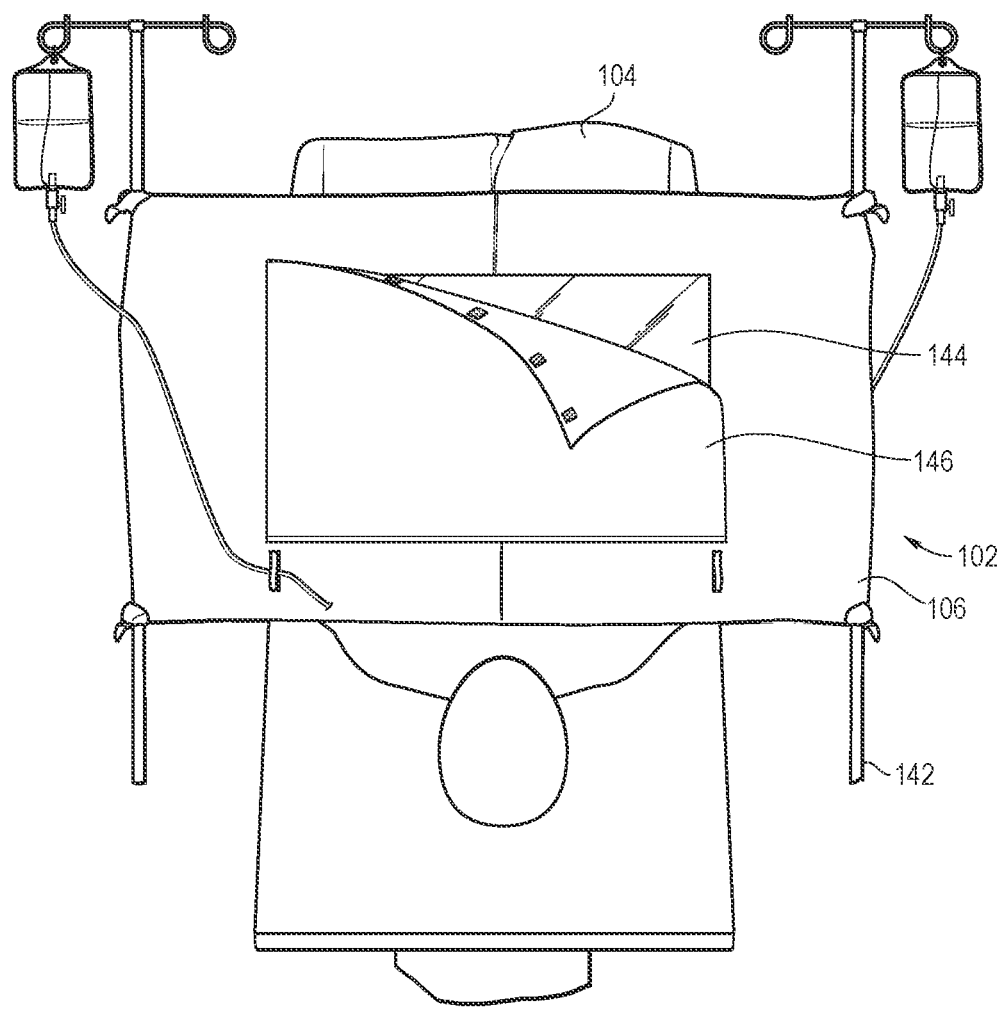
FIG. 3 is a second perspective view showing the upper body portion of a patient during the Cesarean delivery depicted in FIG. 2.

FIGS. 1-3 show an example of a surgical drape 102 in accordance with certain aspects of the present disclosure. Referring to FIGS. 1-3, the surgical drape 102 may include one or more drape sheets, in this case a main portion 104 and a screen portion 106. The main portion 104 and the screen portion 106 may be secured to one another (e.g., via sewing, an adhesive, or another suitable means), or not. During a C-section, the main portion 104 may be laid over the patient's body as shown in FIG. 2. Since the mother is often awake during the procedure, the screen portion 106 may form a barrier field between the operation site and the mother's face.

The main portion 104 may include a surgical opening 108, also referred to as a surgical fenestration, which is configured (e.g., sized, shaped, and positioned) for providing surgical access to the patient's body through the main portion 104. For example, during a C-section, the surgical opening 108 may be positioned relative to the patient's body such that access is provided to a first target patient site 110 at the patient's abdomen. Optionally, the surgical opening 108 may be covered with a flexible adhesive or film, such as an "incise film" known in the industry (e.g., formed with polyurethane or another suitable material) and/or a liner (not shown). If an incise film is included, it may completely cover the surgical opening 108, or alternatively it may include its own fenestrations such that the patient's skin is immediately exposed when the main portion 104 is place over the patient's body. While not required, the optional incise film may be secured to the patient's skin via an adhesive such that it remains in an appropriate position relative to the first target patient site 110 during the C-section.

The main portion 104 may also include a window 112, which is depicted in FIGS. 1-2. The window 112 may be located adjacent to the surgical opening 108, for example. In particular, the window 112 may be located closer to a foot end 114 of the main portion 104 than the surgical opening 108, and the surgical opening 108 may be located closer to a head end 116 of the main portion 104 than the window 112. While the window 112 is shown as having a rectangular shape, other shapes are alternatively contemplated. In the depicted example, the window 112 has a width of about 39 inches and a height of about 16.5 inches, but other dimensions are alternatively contemplated.

While a window may simply be an opening/fenestration through the main portion 104, the window 112 or the present embodiment includes a transparent panel 118. The transparent panel 118 may cover the opening in the main portion 104 such that body fluids or other substances cannot flow through the window 112. The transparent panel 118 may be secured permanently to the surrounding area of the main portion 104 in a fluid-tight manner, for example via sewing the transparent panel 118 around the perimeter of the window 112, using an adhesive, via staples or other mechanical devices, or with any other suitable device or technique.

Advantageously, the window 112 may provide visual access to a second target patient site 120. For example, the second target patient site 120 may be the groin area and/or vaginal area of a patient during a C-section. Advantageously, the medical professionals and/or other personnel may have the ability to visually monitor the second target patient site 120 for abnormalities, such as abnormal blood loss or the flow of other body fluids. While not required, it is also contemplated that a camera may monitor the second target patient site 120 through the window 112.

The window 112 may be selectively coverable by a flap 122. In some embodiments, the flap 122 may be completely removable from the remainder of the main portion 104. However, in the depicted embodiment, the flap 122 is secured to the main portion 104 such that it cannot be removed during typical use. In particular, the flap 122 has a first edge 124 that is secured along the window 112 (e.g., at a seam 125). The securement between the flap 122 at the first edge 124 may be accomplished with any suitable device and/or technique, such as via the use of sewing, adhesive(s), Velcro®, fusing or other heat bonding, etc.

As shown, at least a second edge 126 of the flap 122 may be movable relative to the window 112 such that the flap 122 is movable between a state where it covers the window 112 and a state where the window 112 remains uncovered by the flap 122. The second edge 126 of the flap 122 may include one or more devices for attaching the second edge 126 to another area of the main portion 104. These securement device(s) may include any suitable structure, such as Velcro®, an adhesive, a mechanical device (such as a zipper), etc. To illustrate, FIG. 2 shows a first set of Velcro® areas 128 located at the second edge 126 of the flap 122 and on a first face 132 of the flap 122. A corresponding second set of Velcro® areas 130 is located between the window 112 and the surgical opening 108. Coupling the first set of Velcro® areas 128 to the second set of Velcro® areas 130 may secure the flap 122 in a state such that it covers the window 112. Such a state is advantageous where the patient desires privacy in time periods where a medical professional's visual access of the second target patient area 120 is not necessary, such as when the C-section has not yet begun or has ended, and/or when patient's guests are in the room.

While not shown, the flap 122 may additionally or alternatively include a similar securement device on its second face (which is the opposite face relative to the first face 132). For example, the second edge 126 may include Velcro® on both sides (along with corresponding Velcro® placed in appropriate areas of the main portion 104) such that the flap 122 can be selectively secured in an open state and also a closed state.

In some embodiments, the flap 122 may include a second function beyond simply selectively covering the window 112. For example, the flap 122 may include a material that repels liquid to prevent liquid pooling, thereby limiting or preventing "strikethrough" or leakage through the main portion 104. Alternatively, it is contemplated that the flap 122 may include an absorbent material to absorb liquids for a similar purpose. In another example (or as an addition), the flap 122 may be respectively rigid relative to other portions of the main portion 104 such that the flap 122 provides a suitable surface for placing surgical tools or even a newborn immediately following the delivery stage of the C-section.

Optionally, the main portion 104 may include one or more access structures positioned adjacent to the window 112, as shown in FIG. 2. For example, the access structures may include perforated strips 138 located adjacent to the window 144. While any suitable location and orientation are contemplated, the depicted perforated strips 138 extend from edges of the window 112 towards outer edges of the main portion 104 of the surgical drape 102. In the depicted example, the perforated strip 138 extend to a perimeter edge of the window 112, and are located below (e.g., closer to the foot end 114 of the main portion 104) the abdomen of the patient (e.g., approximately near the patient's thigh or knee), but other arrangements are also possible. Prior to tearing, the perforated strip 138 may include a material that is generally continuous with the remainder of the main portion 104 that prevent liquids from leaking through the base sheet in a default state (e.g., prior to tearing the perforations). Advantageously, the perforated strip 138 may provide a passage to a location beneath the main portion 104 such that a patient can be accessed with a catheter 140 in the groin or vaginal region of the patient, for example. Additionally or alternatively, the perforated strip 138 may be designed such that they provide direct physical or surgical access for a medical professional. The perforated strip 138 may be located in any other suitable position(s).

Optionally, the main portion 104 may include one or more fastening features, such as a strap 150. As an alternative (or in addition), the fastening feature may include something other than a strap, such as a clamp, an area of exposed adhesive, a loop, hook, opening, etc. In the depicted example of FIG. 1, the strap 150 may hold a catheter 152 or another medical device. The strap 150 may be located adjacent to the window 112, as shown, which may be advantageous where the window 112 is used to view the installation and/or continued use of such a device in a location beneath the surgical drape 102. FIG. 2 shows the strap 150 in a different location (e.g., adjacent to the perforated strip 138), which may be advantageous when the strap 150 secures a medical device in place that utilizes the perforated strip 138.

Referring to FIGS. 2-3, the screen portion 106 may be configured to provide a barrier between a patient's head and the first target patient site 110. Optionally, the screen portion 106 may be held in a vertical orientation with one or more support poles 142 or other support members. As shown in FIG. 3, the screen portion 106 may include a window 144 that provides the patient with a field of view towards the area of newborn delivery. Like the window 112 discussed above, the window 144 may include a transparent panel that is secured around its outer perimeter to the remainder of the screen portion 106. Optionally, such a transparent window may be removable and/or at least partially detachable, which may be advantageous when it is desirable to pass a newborn towards a mother's arms, for example.

Additionally or alternatively, the screen portion 106 may include a flap 146 for covering the window 144, which may be selectively opened or closed (e.g., in a manner similar to the flap 122 shown in FIGS. 1-2). While the flap 146 is on the patient side of the screen portion 106 in the depicted embodiment (and therefore capable of being opened and closed by the patient), the flap 146 may alternatively be on the opposite side such that it is controlled by the medical team, which may be advantageous where the medical professional(s) do not want the patient to view one or more steps of the C-section, and/or to protect the patient's eyes from bright overhead lights used during the surgery. In certain embodiments, flaps may be located on both sides of the screen portion 106 or excluded altogether, for example.

While various embodiments have been described, it will be apparent to those of ordinary skill in the art that many more embodiments and implementations are possible. Accordingly, the embodiments described herein are examples, not the only possible embodiments and implementations.

Having described various aspects of the subject matter above, additional disclosure is provided below that may be consistent with the claims originally filed with this disclosure. In describing this additional subject matter, reference may be made to the previously described figures. Any of the following aspects may be combined, where compatible.

In a first aspect, a surgical drape may include one or more of the following: a main portion, the main portion having a surgical opening, the surgical opening being configured to provide surgical access to a first target patient site; a window located adjacent to the surgical opening, the window including a transparent panel such that the window provides visual access to a second target patent site; and a flap having at least one edge secured to the main portion, where the flap includes a second edge that is movable such that the flap selectively covers the window.

The window may be located such that the visual access is provided to a patient's vaginal area during a Cesarean section. The surgical opening may be located such that it provides surgical access to at least one of an abdomen and a uterus of the patient.

The second edge of the flap may include at least one attachment device such that the second edge is selectively securable in a state covering the window. The at least one attachment device may include a Velcro® surface that is configured to engage a second Velcro® surface located on at least one of the main portion and the transparent panel of the window. A third Velcro® surface may be located on the main portion such that the second edge of the flap is securable in a second state where the window is uncovered by the flap.

The flap may include a material that is rigid relative to the main portion for providing a working surface for receiving and supporting at least one surgical tool.

The surgical drape may further include an access structure located adjacent to the window and configured to provide at least one of catheter access and physical access to a second target patient site.

The access structure may include a perforated strip extending through the main portion.

The surgical drape may further include a screen portion having a second window, the second window being configured for providing a patient with a view towards a second target patient site.

In a second aspect, a surgical drape may include one or more of the following: a main portion, the main portion having a surgical opening, the surgical opening being configured to provide surgical access to a first target patient site; and a window located adjacent to the surgical opening, the window including a transparent panel such that the window provides visual access to a second target patent site.

The window may be located such that the visual access is provided to a patient's vaginal area during a Cesarean section. The surgical opening may be located such that it provides surgical access to at least one of an abdomen and a uterus of the patient.

The flap may include a material that is rigid relative to the main portion for providing a working surface for receiving and supporting at least one surgical tool.

An access structure may be located adjacent to the window and configured to provide at least one of catheter access and physical access to a second target patient site. The access structure, if included, may include a perforated strip extending through the main portion.

In a third aspect, a surgical drape may include one or more of the following: a main portion, the main portion having a surgical opening, the surgical opening being configured to provide surgical access to at least one of an abdomen and a uterus of a patient; and a window located adjacent to the surgical opening, the window including a transparent panel such that the window provides visual access to a vaginal area of the patient.

A screen portion of the surgical drape may have a second window, the second window being configured for providing a patient with a view towards a second target patient site. The second window may include a flap that is selectively openable and closeable.

A perforated strip through the main portion may extend in an area adjacent to the window.

We claim:

1. A surgical drape, comprising:
   a main portion,
   the main portion having a surgical opening;
   a window located adjacent to the surgical opening, the window including a transparent panel; and
   a flap having a first edge secured to the main portion,
   wherein the flap includes a second edge that is movable such that the flap selectively covers the window;
   wherein the window is configured to be located in a vaginal area of a patient during a Cesarean section procedure such that the window provides visual access to the vaginal area during the Cesarean section procedure, and
   wherein the surgical opening is configured to be located in at least one of an abdomen area and a uterus area of the patient during the Cesarean section procedure such that the surgical opening provides surgical access to at least one of an abdomen and a uterus of the patient during the Cesarean section procedure.

2. The surgical drape of claim 1, further comprising an access structure located adjacent to the window and configured to provide at least one of catheter access and physical access.

3. The surgical drape of claim 2, wherein the access structure includes a perforated strip extending through the main portion.

4. The surgical drape of claim 1, wherein the second edge of the flap includes at least one attachment device such that the second edge is selectively securable covering the window.

5. The surgical drape of claim 4, wherein the at least one attachment device includes a first hook and loop surface that is configured to engage a second hook and loop surface located on at least one of the main portion and the transparent panel of the window.

6. The surgical drape of claim 5, wherein a third hook and loop surface is located on the main portion such that the second edge of the flap is securable onto the main portion when the window is uncovered by the flap.

7. The surgical drape of claim 1, wherein the flap includes a material that is rigid relative to the main portion for providing a working surface for receiving and supporting at least one surgical tool.

8. The surgical drape of any of claim 1, further comprising a screen portion having a second window, the second window being configured for providing the patient with a view.

* * * * *